(12) United States Patent
McClintock et al.

(10) Patent No.: US 8,506,603 B2
(45) Date of Patent: Aug. 13, 2013

(54) SURGICAL ROD SCORER AND METHOD OF USE OF THE SAME

(75) Inventors: Larry McClintock, Gore, VA (US);
Kevin R Strauss, Leesburg, VA (US);
Faheem Sandhu, Washington, DC (US)

(73) Assignee: K2M, Inc., Leesburg, VA (US)

(*) Notice: Subject to any disclaimer, the term of this patent is extended or adjusted under 35 U.S.C. 154(b) by 0 days.

(21) Appl. No.: 13/170,859

(22) Filed: Jun. 28, 2011

(65) Prior Publication Data

US 2011/0253760 A1  Oct. 20, 2011

Related U.S. Application Data

(63) Continuation-in-part of application No. 12/904,817, filed on Oct. 14, 2010.

(60) Provisional application No. 61/278,924, filed on Oct. 14, 2009.

(51) Int. Cl.
*A61B 17/70* (2006.01)

(52) U.S. Cl.
USPC .................................. 606/279; 606/86 A

(58) Field of Classification Search
CPC .................. A61B 17/7074; A61B 17/7079
USPC ........................................ 606/254–279, 86 A
See application file for complete search history.

(56) References Cited

U.S. PATENT DOCUMENTS

| | | | |
|---|---|---|---|
| 1,435,467 A | 11/1922 | Harman | |
| 1,674,440 A | 6/1928 | McCloskey | |
| 1,945,949 A | 2/1934 | Myers | |
| 2,016,735 A | 10/1935 | Abramson et al. | |
| 2,271,033 A | 1/1942 | Petersen | |
| 2,283,572 A | 5/1942 | Peterson | |
| 2,325,353 A | 7/1943 | Wright | |
| 2,350,667 A | 6/1944 | Bates | |
| 2,360,887 A | 10/1944 | Parker | |
| 2,379,177 A | 10/1945 | Pavey | |
| 2,491,543 A | 12/1949 | Alfonso | |
| D158,536 S | 5/1950 | Wolcott | |
| 2,511,358 A | 6/1950 | Mayer et al. | |
| 2,526,471 A | 10/1950 | Ginns | |
| 2,556,974 A | 6/1951 | Nye, Jr. | |
| 2,557,737 A | 6/1951 | Franck | |
| 2,582,406 A | 1/1952 | Bachli et al. | |
| 2,629,926 A | 3/1953 | Franck | |
| 2,630,028 A | 3/1953 | McIntosh | |
| 2,630,029 A | 3/1953 | Franck | |

(Continued)

OTHER PUBLICATIONS

International Search Report and Written Opinion of the International Searching Authority mailed Dec. 2, 2010 in counterpart International Application No. PCT/US2010/052693 filed Oct. 14, 2010.

*Primary Examiner* — Ellen C Hammond
(74) *Attorney, Agent, or Firm* — Carter, DeLuca, Farrell & Schmidt, LLP

(57) ABSTRACT

A method for cutting surgical rod in situ is provided. The method includes positioning an operable end of a surgical rod scorer around surgical rod that has been previously affixed to a spinal segment via at least two pedicle screws. A portion of the surgical rod is scored with the surgical rod scorer. The scored surgical rod is grasped with a surgical rod bender. And, the scored surgical rod is bent such that the surgical rod separates along the scored portion of the surgical rod.

20 Claims, 10 Drawing Sheets

(56) References Cited

U.S. PATENT DOCUMENTS

| | | | |
|---|---|---|---|
| 2,666,984 | A | 1/1954 | Shafer |
| 2,706,853 | A | 4/1955 | Wilson |
| 2,716,280 | A | 8/1955 | Ruhe |
| 2,718,058 | A | 9/1955 | Arnold |
| 2,747,275 | A | 5/1956 | Jonasson |
| 2,787,054 | A | 4/1957 | Franck |
| 2,796,663 | A | 6/1957 | Karnes |
| 2,814,867 | A | 12/1957 | Charles |
| 2,817,898 | A | 12/1957 | Vermette |
| 2,870,535 | A | 1/1959 | Vermette |
| 2,871,733 | A | 2/1959 | Lauck |
| 2,875,518 | A | 3/1959 | Dyczynski |
| 2,877,549 | A | 3/1959 | Landreth |
| 2,993,274 | A | 7/1961 | Dirks |
| 3,008,231 | A | 11/1961 | Caproni |
| 3,013,335 | A | 12/1961 | Kowal |
| 3,022,575 | A | 2/1962 | Wright |
| 3,031,237 | A | 4/1962 | Weibel |
| 3,070,885 | A | 1/1963 | Musy et al. |
| 3,082,523 | A | 3/1963 | Modes et al. |
| 3,097,428 | A | 7/1963 | Lutsker |
| 3,100,934 | A | 8/1963 | Jonasson |
| 3,106,776 | A | 10/1963 | Plas |
| 3,117,375 | A | 1/1964 | Meese |
| 3,118,227 | A | 1/1964 | Samuels et al. |
| 3,171,199 | A | 3/1965 | Meese |
| 3,196,652 | A | 7/1965 | Meese |
| 3,237,301 | A | 3/1966 | Wilson |
| 3,240,088 | A | 3/1966 | Samuels et al. |
| 3,376,638 | A | 4/1968 | Bjalme et al. |
| 3,403,442 | A | 10/1968 | Reese et al. |
| 3,408,738 | A | 11/1968 | Schade |
| 3,520,057 | A | 7/1970 | Gore et al. |
| 3,545,081 | A | 12/1970 | Butler |
| 3,608,194 | A | 9/1971 | Miller |
| 3,624,682 | A | 11/1971 | Kowal |
| 3,651,569 | A | 3/1972 | Arnot |
| 3,885,261 | A | 5/1975 | Skvarenina |
| 3,932,937 | A | 1/1976 | Bastiansen |
| 4,078,304 | A | 3/1978 | Netzel |
| 4,103,419 | A | 8/1978 | Matthews et al. |
| 4,114,485 | A | 9/1978 | Coblitz et al. |
| 4,132,100 | A | 1/1979 | Schuler |
| 4,174,646 | A | 11/1979 | Kotler |
| 4,177,557 | A | 12/1979 | Courty |
| 4,305,205 | A | 12/1981 | Girala |
| 4,345,376 | A | 8/1982 | Benson et al. |
| 4,438,562 | A | 3/1984 | Courty |
| 5,099,577 | A | 3/1992 | Hutt |
| 5,203,083 | A | 4/1993 | Domonoske |
| 5,206,996 | A | 5/1993 | McDaniel |
| 5,230,150 | A | 7/1993 | Sperti |
| 5,345,682 | A | 9/1994 | Dubinsky et al. |
| 5,414,932 | A | 5/1995 | Azkona |
| 5,513,434 | A * | 5/1996 | Hamman ............... 30/101 |
| 5,515,609 | A | 5/1996 | Sperti |
| 5,903,980 | A | 5/1999 | Collier et al. |
| 5,943,778 | A | 8/1999 | Alana |
| 5,988,027 | A | 11/1999 | Lenox |
| 6,055,732 | A | 5/2000 | Hu |
| 6,134,997 | A | 10/2000 | Rosanova |
| 6,202,307 | B1 | 3/2001 | Wrate |
| 6,226,823 | B1 | 5/2001 | Ma Gee |
| 6,237,449 | B1 | 5/2001 | Orlosky |
| 6,393,700 | B1 | 5/2002 | Babb |
| 6,401,340 | B1 | 6/2002 | King |
| 6,609,302 | B2 | 8/2003 | Welker et al. |
| 6,658,739 | B1 | 12/2003 | Huang |
| 6,739,055 | B2 | 5/2004 | Lee |
| 7,275,320 | B2 | 10/2007 | Lee |
| RE40,461 | E | 8/2008 | Hu |
| 7,591,072 | B2 | 9/2009 | Stravitz |
| 7,934,317 | B2 | 5/2011 | Chiu |
| 2002/0121173 | A1 | 9/2002 | Filipo |
| 2005/0125986 | A1 | 6/2005 | Pham et al. |
| 2005/0203513 | A1* | 9/2005 | Jahng et al. ............ 606/61 |
| 2005/0274022 | A1 | 12/2005 | Korczak et al. |
| 2007/0209495 | A1 | 9/2007 | Marcon |
| 2007/0251095 | A1 | 11/2007 | Nagasoe |
| 2007/0270843 | A1* | 11/2007 | Matthis et al. ............ 606/61 |
| 2008/0000091 | A1 | 1/2008 | Eriguchi |
| 2008/0060203 | A1 | 3/2008 | Metcalf |
| 2009/0049697 | A1 | 2/2009 | Williams |
| 2009/0076549 | A1* | 3/2009 | Lim et al. ............ 606/246 |
| 2009/0090008 | A1 | 4/2009 | Nagasoe |
| 2010/0088898 | A1 | 4/2010 | Thorson et al. |
| 2010/0160967 | A1* | 6/2010 | Capozzoli ............ 606/256 |
| 2010/0199499 | A1 | 8/2010 | Dibble |
| 2010/0205809 | A1 | 8/2010 | Lier et al. |
| 2011/0107601 | A1* | 5/2011 | Crainich et al. ............ 30/95 |

\* cited by examiner

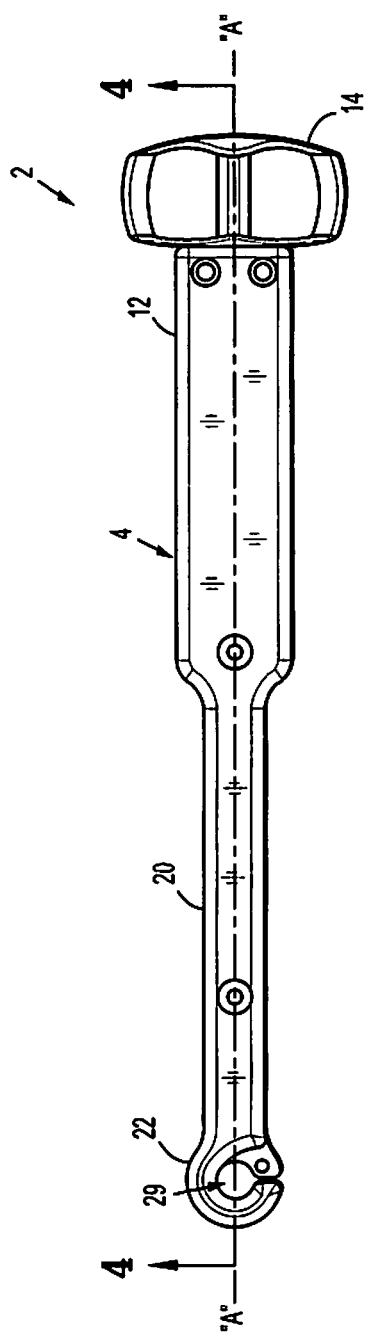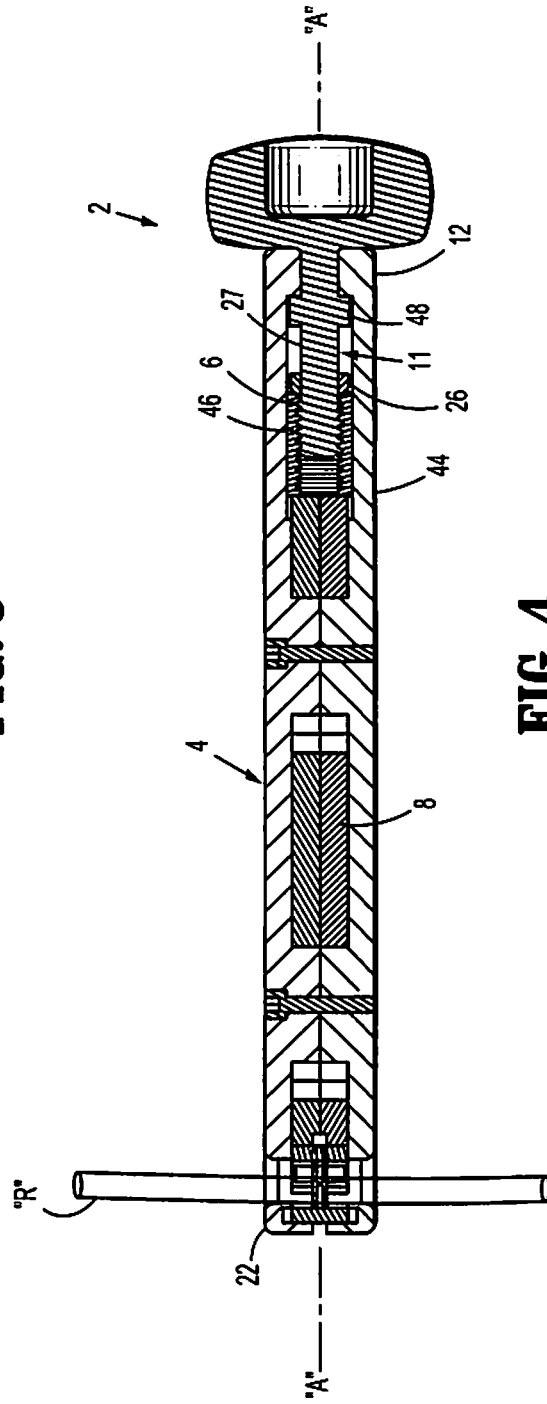

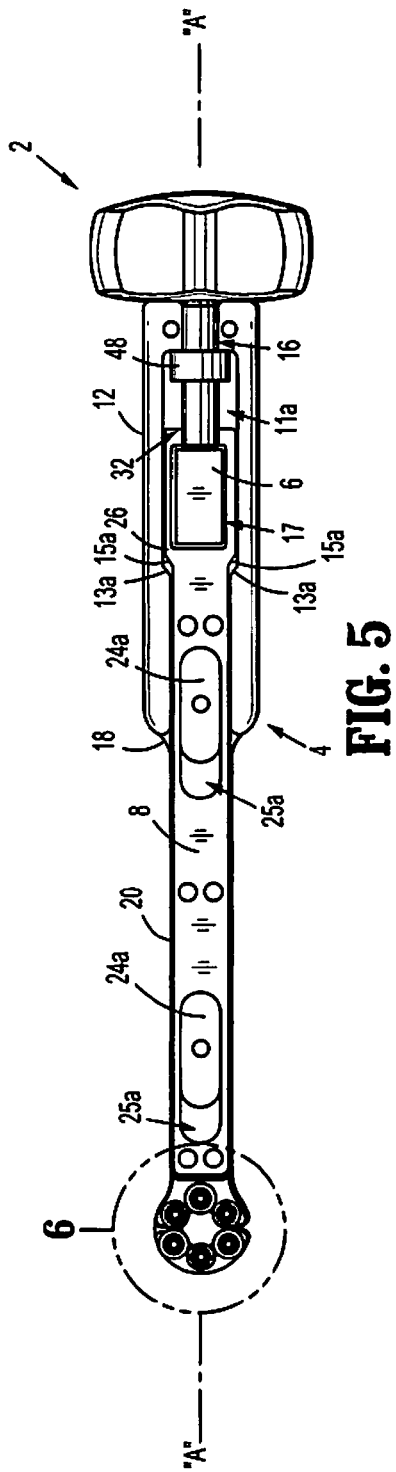
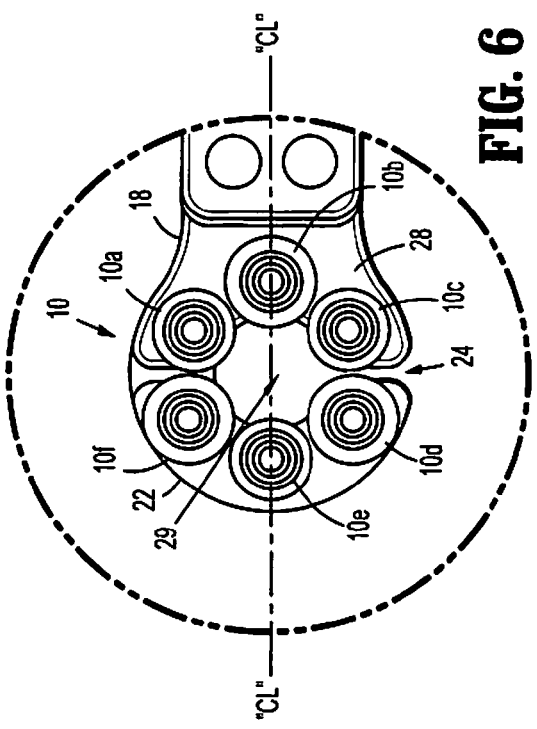

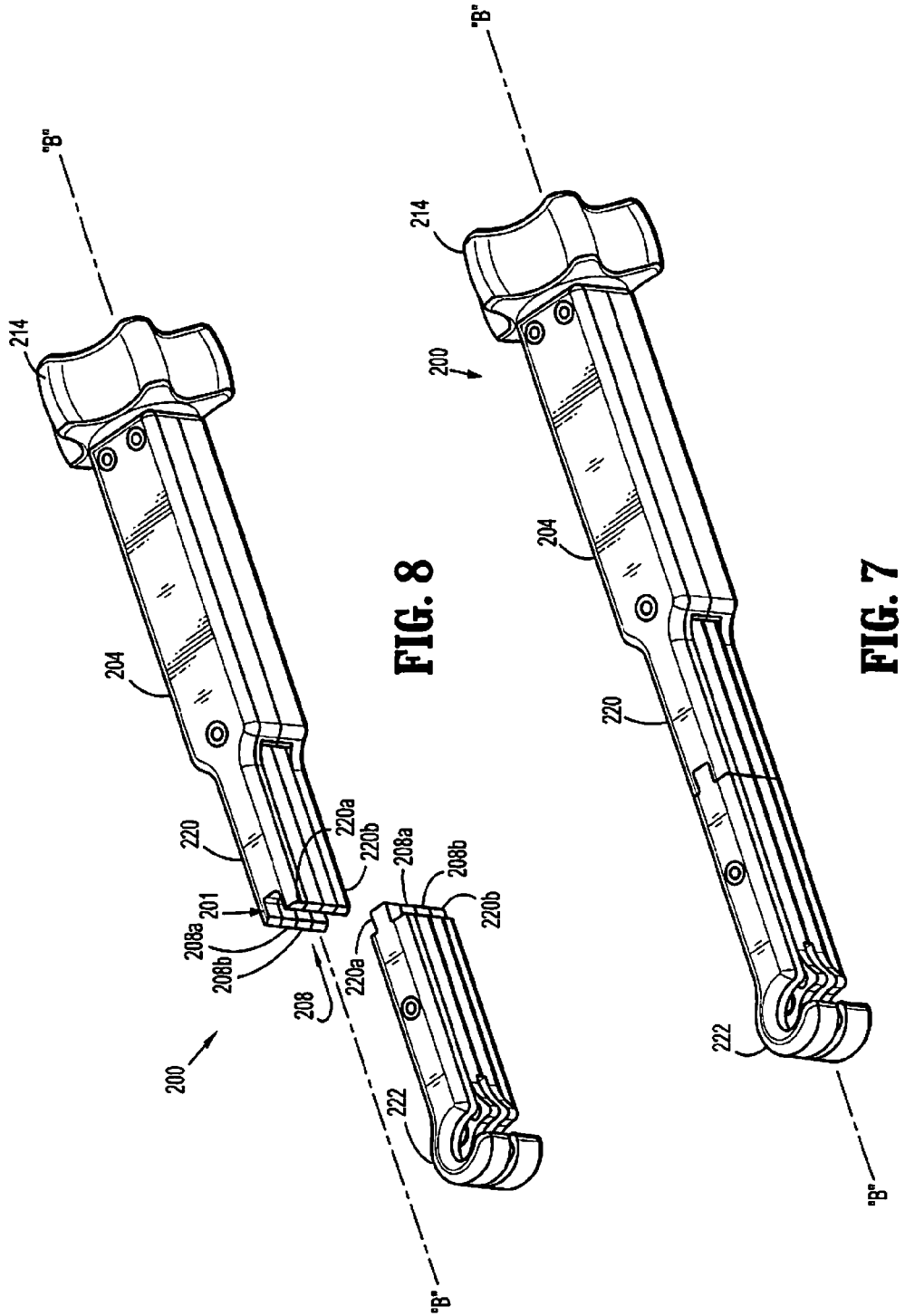

SURGICAL ROD SCORER AND METHOD OF USE OF THE SAME

CROSS-REFERENCE TO RELATED APPLICATIONS

The present application is a continuation-in-part of pending U.S. patent application Ser. No. 12/904,817 to McClintock et al., filed on Oct. 14, 2010, which claims the benefit of and priority to U.S. Provisional Application No. 61/278,924 to McClintock et al., filed on Oct. 14, 2009, the entire contents of each of these applications is incorporated by reference herein.

BACKGROUND

1. Technical Field

The present disclosure relates to a surgical rod scorer and method of use of the same. More particularly, the present disclosure relates to a surgical rod scorer including a plurality of cutting elements aligned along a common scoring axis of the surgical rod scorer.

2. Description of Related Art

Disease, the effects of aging, or physical trauma resulting in damage to the spine has been treated in many instances by fixation or stabilization of the affected vertebra. A wide variety of spinal fixation apparatuses have been employed in surgical procedures for correcting spinal injuries and the effects of spinal diseases. Many types of spinal fixation apparatuses typically use a pair of longitudinal surgical rods running in a relatively parallel relationship to each other and the spinal column. The surgical rods are often bent into various complex shapes to provide the desired correction to a patient's anatomy. Typically, the surgical rods are solid.

In certain instances, the surgical rods may need to be cut. For example, typically, the surgical rods are longer than necessary in order to allow for the variability of a patient's anatomy and, therefore, need to be cut once a construct, e.g., a spinal fixation apparatus, is completed. Also, the surgical rods may need to be cut in revision surgeries where the hardware of the construct that was implanted needs to be removed so additional hardware can be implanted and/or additional corrections can be made. In either of the foregoing cutting scenarios involving surgical rods, it may prove advantageous to transfer minimal force to the construct and/or surrounding anatomy and to provide a smooth edge to the cut rod so it does not damage surrounding tissue and vasculature.

Conventional devices employed to cut the surgical rods utilize a "bolt cutter" approach, see U.S. Pat. No. 5,836,937 issued to Holmes. Typically, devices of this type include a surgical rod cutter having a set of jaw members rotatably connected to one another. The jaw members are capable of opening and closing upon actuation thereof. Each of the jaw members includes a cutting blade that opposes a cutting edge on the other jaw member. However, this type of rod cutter applies a large amount of force to the surgical rod, which, in turn, effectively shears the surgical rod apart; this type of rod cutter does not provide a clean cut of the surgical rod. That is, this force is, typically, applied to a portion of rod that is to be removed and, thus, creates a burr on a cut edge of the surgical rod after the surgical rod is cut.

SUMMARY

The present disclosure provides a method for cutting surgical rod in situ. The method includes positioning an operable end of a surgical rod scorer around surgical rod, such as, for example, a titanium, titanium alloy, cobalt, chrome, or stainless steel solid surgical rod that has been previously affixed to a spinal segment via two or more bone anchors including, but not limited to pedicle screws, hooks and the like. Subsequently, a portion of the surgical rod is scored with the surgical rod scorer. Thereafter, the scored surgical rod is grasped with a surgical rod bender, and, the scored surgical rod is bent such that the surgical rod separates along the scored portion of the surgical rod.

In embodiments the surgical rod scorer includes a handle having an elongated shaft. The shaft extends from the handle and defines a longitudinal axis through the handle. A proximal end of the handle is configured to support a knob that is rotatable about the longitudinal axis and fixed from translation along the longitudinal axis. An operable head disposed at a distal end of the shaft is configured to support one or more cutting elements. The operable head of the shaft has an opening that is configured for insertion of a surgical rod therethrough. A reciprocating member operably disposed and translatable within the handle and the shaft of the surgical rod scorer is translatable along the longitudinal axis. The reciprocating member includes proximal and distal ends. The proximal end of the reciprocating member is in mechanical communication with the knob. The distal end of the reciprocating member is configured to support one or more cutting elements. A drive member operably coupled to the proximal end of the reciprocating member and to the knob is configured to translate the reciprocating member along the longitudinal axis. Rotation of the knob about the longitudinal axis translates the reciprocating member including the one or more cutting elements supported thereon from a retracted position, to one or more extended positions for scoring the surgical rod inserted through the opening of the operable head of the shaft.

BRIEF DESCRIPTION OF THE DRAWINGS

Various embodiments of the present disclosure are described herein with reference to the drawings wherein:

FIG. 3 is a top elevation view of the surgical rod scorer depicted in FIG. 1;

FIG. 4 is a cross-sectional view of the surgical rod scorer depicted in FIG. 3 taken along section line 4-4;

FIG. 5 is a partial cut-away top view of the surgical rod scorer depicted in FIG. 3 with a reciprocating member of the surgical rod scorer in an extended position;

FIG. 6 is an enlarged view of the area of detail depicted in FIG. 5;

FIG. 7 is a perspective view of a surgical rod scorer according to another embodiment of the present disclosure;

FIG. 8 is a perspective view of the surgical rod scorer depicted in FIG. 7 with an operable end of the surgical rod scorer unattached from a handle of the surgical rod scorer;

DETAILED DESCRIPTION

In the following description, as is traditional, the term "proximal" refers to a portion of a surgical instrument closer to the operator while the term "distal" refers to a portion of a surgical instrument farther from the operator. In addition, the term "cephalad" is used in this application to indicate a direction toward a patient's head, whereas the term "caudad" indicates a direction toward the patient's feet. Further still, for the purposes of this application, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front. In the following description, well-known functions or constructions are not described in detail to avoid obscuring the present disclosure in unnecessary detail.

Figure 1:
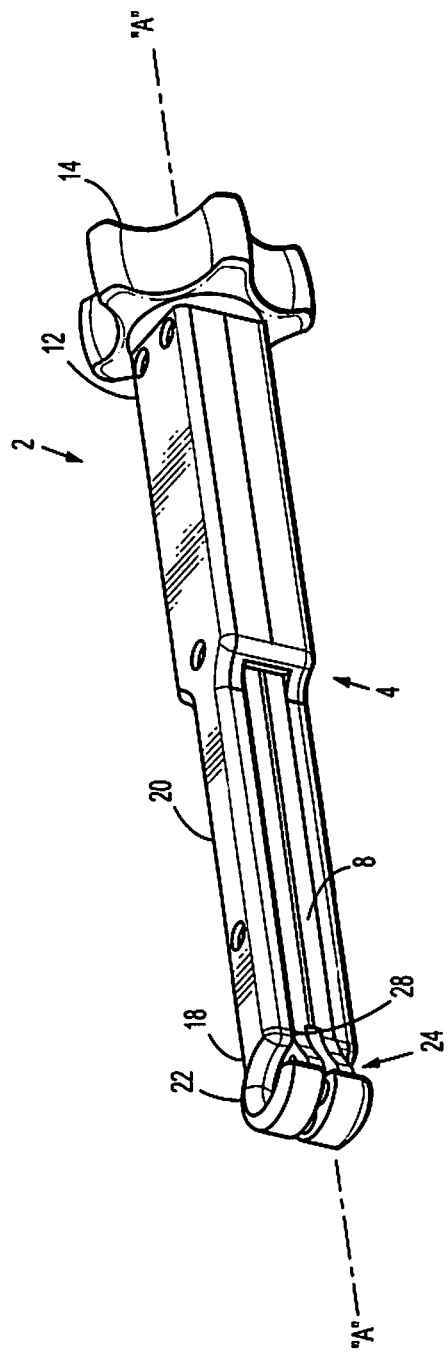
FIG. 1 is a perspective view of a surgical rod scorer according to an embodiment of the present disclosure.

With reference to FIGS. 1-6, and initially with reference to FIG. 1, a surgical rod scorer 2 according to an embodiment of the present disclosure is shown. The surgical rod scorer 2 is configured to score a surgical rod "R" (see FIGS. 4 and 10). The surgical rod scorer 2 may be utilized to score a surgical rod "R" prior to fixating the surgical rod "R" in a patient, or subsequent to fixation thereto, e.g., in-situ.

With continued reference to FIG. 1, the surgical rod scorer 2 is illustrated in an assembled configuration. In the assembled configuration, the surgical rod scorer 2 includes a handle 4. Handle 4 includes a proximal end 12. Proximal end 12 is configured to rotatably support a knob 14. A shaft 20 extends from the proximal end 12 and has a generally elongated configuration. A longitudinal axis "A-A" is defined through the handle 4 and the shaft 20. The shaft 20 includes a distal end 18 that supports a working or operable head 22. A drive member 6 (FIG. 2) is housed within the handle 4 and is configured to translate a reciprocating member 8 from a retracted position, to an extended position. One or more cutting elements 10 (FIG. 6) are operably coupled to each of the operable head(s) 22 of the shaft (cutting wheels 10d-10f are operably coupled to the operable head 22) and reciprocating member 8 (cutting wheels 10a-10c are operably coupled to the reciprocating member 8).

Figure 2:
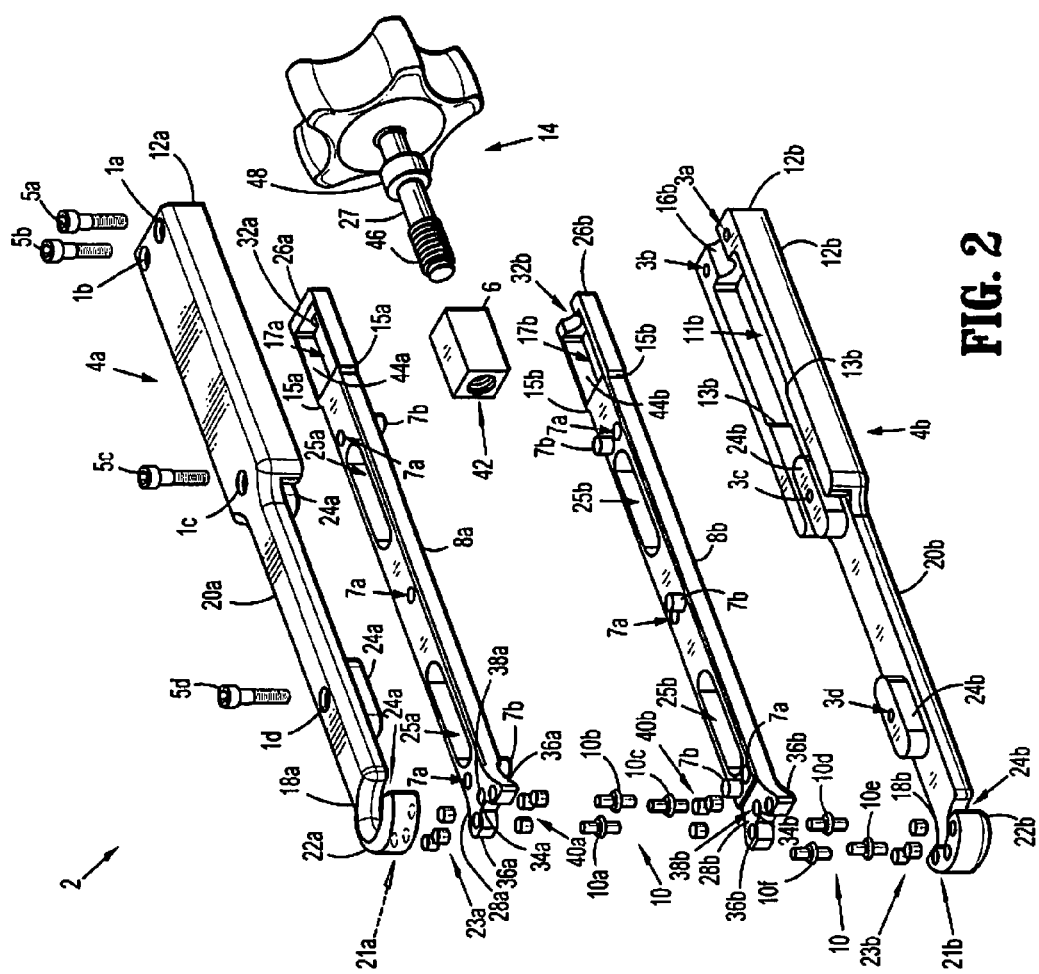
FIG. 2 is an exploded view of the surgical rod scorer depicted in FIG. 1 with components separated.

FIG. 2 illustrates an exploded view of the surgical rod scorer 2 with the parts separated. As illustrated in FIG. 2, the handle 4 includes two substantially identical handle half portions 4a and 4b that are operably coupled to one another via one or more suitable coupling methods. In the illustrated embodiments, handle half portions 4a and 4b are held in an assembled configuration via screws, i.e., handle half portions 4a and 4b are screwed together (FIG. 1). More particularly, handle half portion 4a includes four apertures 1a-1d that are in vertical alignment with four corresponding threaded apertures 3a-3d operably disposed on the handle halve portion 4b (FIG. 2). Four screws 5a-5d are receivable within the four apertures 1a-1d on the handle half portion 4a and are configured to engage the four threaded apertures 3a-3d on the handle half portion 4b.

Handle half portions 4a and 4b each include respective proximal ends 12a and 12b. In the assembled configuration, the proximal ends 12a and 12b collectively define or form the proximal end 12 of the handle 4 (see FIG. 1 in combination with FIG. 2). In the assembled configuration, proximal end 12 of the handle 4 is configured to rotatably support the knob 14 thereabout (FIGS. 1 and 3-5). Specifically, an aperture or opening 16 (FIG. 5) of suitable proportion is operably disposed at the proximal end 12 (the opening 16 is shown engaged with a shaft 27 of the knob 14 and as such the opening 16 is not visible). More specifically, in the assembled configuration, opening 16 is defined by a semi-circular notch 16b (FIG. 2) disposed at the proximal end 12b and a semi-circular notch (not explicitly shown) disposed at the proximal end 12a. Opening 16 is configured to maintain the knob 14 in a fixed orientation along the longitudinal axis "A-A" while the knob 14 is rotated such that the drive member 6 is movable with respect to the knob 14 and along the longitudinal axis "A-A," described in greater detail below.

Each of the respective proximal ends 12a and 12b includes a respective cavity 11a and 11b, see FIGS. 2 and 5. In the assembled configuration the cavities 11a and 11b collectively define or form a cavity 11 that is configured to house a portion of the reciprocating member 8 including the drive member 6 therein such that the reciprocating member 8 including the drive member 6 is translatable within the cavity 11 from the retracted position, to the extended position when the knob 14 is rotated. Each of the cavities 11a and 11b includes a respective pair of shoulders 13a (FIG. 5) and 13b (FIG. 2) that are configured to contact a corresponding pair of flanges 15a and 15b that are formed adjacent respective proximal ends 26a and 26b of reciprocating member half portions 8a and 8b (FIG. 2) when the reciprocating member 8 has translated a predetermined distance distally. This predetermined distance corresponds to the cutting elements 10a-10c on the reciprocating member 8 being positioned adjacent the cutting elements 10d-10f on the operable end 22, as best seen in FIG. 6.

To facilitate gripping the handle 4, an exterior surface of the handle 4 may be textured or otherwise treated. For example, in one particular embodiment, the exterior surface of the handle half portion 4a may include a plurality of raised projections or may include a knurled surface.

With continued reference to FIG. 2, handle half portions 4a and 4b include respective elongated shafts 20a and 20b that taper from the respective proximal ends 12a and 12b. In the assembled configuration the elongated shafts 20a and 20b collectively define or form the shaft 20 (see FIG. 1 for example). Each of the elongated shafts 20a and 20b includes a distal end 18a and 18b. In the assembled configuration, the distal ends 18a and 18b collectively define or form the distal end 18 of the handle 4 (see FIG. 1 in combination with FIG. 2). Each of the respective distal ends 18a and 18b is configured to support a respective operable head half portion 22a and 22b (FIG. 2).

Operable head half portions 22a and 22b may have any suitable shape. In the illustrated embodiments, operable head half portions 22a and 22b include a generally arcuate configuration having a respective notched opening 24a and 24b forming a "hook" or "C" shape (FIGS. 1 and 2). In the assembled configuration, operable head half portions 22a and 22b including their respective notched opening 24a and 24b collectively define or form the operable head 22 with a center opening 29 (FIG. 6) having the notched opening 24 (FIG. 1) that together are configured for insertion of a surgical rod "R"

therethrough. The generally arcuate configuration of the operable end 22 with the notched opening 24 facilitates rotating the handle 4 including the reciprocating member 8 about surgical rod "R" when the surgical rod "R" positioned within the center opening 29 of the operable head 22, see FIG. 4.

Each of the operable head half portions 22a and 22b includes a respective plurality of apertures 21a and 21b (FIG. 2) that is configured to receive corresponding plurality of bushings 23a and 23b. Each of the plurality of bushings 23a and 23b is configured to receive a corresponding one of the one or more cutting elements 10, e.g., cutting wheels 10d-10f. Each of the plurality of bushings 23a and 23b is configured to facilitate rotation of the cutting wheels 10d-10f seated therein when the surgical rod scorer 2 is rotated about surgical rod "R". In certain embodiments, such as, for example, when rotation of the cutting elements is not particularly important, the plurality of apertures 21a and 21b may be configured to directly receive a corresponding one of the one or more cutting wheels 10d-10f.

In the assembled configuration, the operable head half portions 22a and 22b are disposed in a spaced-apart relation with respect to one another to facilitate movement of the one or more cutting wheels 10d-10f. More particularly, the operable head half portions 22a and 22b are spaced from each other at a predetermined distance that allows the one or more of the cutting wheels 10d-10f to rotate about the same scoring axis (FIGS. 1, 4 and 6).

One or more respective guide members 24a and 24b are operably disposed at predetermined locations along an inner facing surface of each of the handle half portions 4a and 4b (FIG. 2); two guide members 24a and two guide members 24b are shown on each of the respective handle half portions 4a and 4b. Each of the guide members 24a and 24b is configured to operably couple to a corresponding slot 25a and 25b operably disposed on respective reciprocating member half portions 8a and 8b of the reciprocating member 8. For illustrative purposes, only guide members 24a are shown operably coupled to the corresponding slots 25a, see FIG. 5 for example. Each of the guide members 24a and 24b is movable within the corresponding slot 25a and 25b and is configured to facilitate movement of the reciprocating member 8 along the longitudinal axis "A-A" and a centerline "CL" (FIG. 6) of the handle 4 when the knob 14 is rotated.

With reference again to FIG. 2, reciprocating member half portions 8a and 8b are illustrated. In the assembled configuration, the reciprocating member half portions 8a and 8b collectively define or form the reciprocating member 8. Reciprocating member 8 includes a generally elongated configuration and is operably disposed and translatable within the handle 4 including the shaft 20 along the longitudinal axis "A-A," (FIGS. 1 and 4-5).

Reciprocating member half portions 8a and 8b operably couple to one another with one or more suitable coupling methods (FIG. 2). In the illustrated embodiment, a "snap-fit" or "press-fit" connection utilizes a plurality of indents 7a and detents 7b (FIG. 2) to couple the reciprocating member half portions 8a and 8b to each other. More particularly, the indents 7a and detents 7b are operably disposed along predetermined locations along an inner facing surface of the reciprocating member half portions 8a and 8b and couple the reciprocating member half portions 8a and 8b to each other.

Each of the reciprocating member half portions 8a and 8b includes respective proximal ends 26a and 26b and respective distal ends 28a and 28b. In the assembled configuration, the proximal ends 26a and 26b collectively define or form a proximal end 26, as best seen in FIG. 5. Likewise, in the assembled configuration, the distal ends 28a and 28b collectively define or form a distal end 28, as best seen in FIG. 1.

The proximal end 26 of the reciprocating member 8 is in mechanical communication with the knob 14. More particularly, in the assembled configuration, proximal end 26 of the reciprocating member 8 is configured to support drive member 6 such that the knob 14 is rotatable relative to the drive member 6 (FIGS. 1 and 3-5). Specifically, an aperture or opening 32 (FIG. 5) of suitable proportion is operably disposed at the proximal end 26 (the opening 32 is shown engaged with the shaft 27 of the knob 14 and as such the opening 32 is not visible). More specifically, in the assembled configuration, opening 32 is defined by a semi-circular notch 32a disposed at the proximal end 26a and a semi-circular notch 32b disposed at the proximal end 26b, as best seen in FIG. 2. Opening 32 is configured to receive the shaft 27 of the knob 14.

The proximal end 26 of the reciprocating member 8 is configured to house the drive member 6 therein. More particularly, each of the respective proximal ends 26a and 26b includes a respective elongated opening 17a and 17b defined by interior walls 44a and 44b, respectively, see FIG. 2. In the assembled configuration, the elongated openings 17a and 17b collectively define or form an elongated opening 17 (FIG. 5 illustrates the drive member 6 engaged in the cavity 17, as such the cavity 17 is not explicitly visible). Opening 17 is configured to house the drive member 6 therein such that the reciprocating member 8 including the drive member 6 is translatable within the cavity 11 of the proximal end 12 of the handle 4 from the retracted position, to the extended position when the knob 14 is rotated. As noted above, contact between the pair of shoulders 13a and 13b (FIGS. 2 and 5) and the corresponding pair of flanges 15a and 15b prevents the reciprocating member 8 from translating distally past a predetermined distance.

Distal ends 28a and 28b may have any suitable shape. In the illustrated embodiment, distal ends 28a and 28b include a generally arcuate configuration. More particularly, each of the distal ends 28a and 28b includes a respective generally concave medial portion 34a and 34b with two respective distally extending fingers 36a and 36b on each side of the concave medial portion 34a and 34b, as best seen in FIG. 2. The generally concave configuration of the distal ends 28a and 28b facilitates rotating the handle 4 including the reciprocating member 8 about surgical rod "R" when the surgical rod "R" is inserted through the notched opening 24.

Each of the distal ends 28a and 28b includes a respective plurality of apertures 38a and 38b (FIG. 2) that is configured to receive a corresponding plurality of bushings 40a and 40b. Each of the plurality of bushings 40a and 40b is configured to receive a corresponding one of the one or more cutting elements 10, e.g., cutting wheels 10a-10c. Other than receiving the respective cutting wheels 10a-10c therein, the plurality of bushing 40a and 40b function in a manner as disclosed above with respect to the plurality of bushing 23a and 23b.

In the assembled configuration, the distal ends 28a and 28b are disposed in a spaced-apart relation with respect to one another to facilitate movement of the one or more cutting wheels 10a-10c. Specifically, the distal ends 28a and 28b are spaced apart from each other at a predetermined distance that allows the one or more of the cutting wheels 10a-10c to rotate about the same scoring axis (FIGS. 1 and 4). More specifically, each of the distal ends 28a and 28b are offset from the respective inner facing surfaces of the reciprocating half portions 8a and 8b, as best seen in FIG. 2 with respect to distal end 28b.

With reference again to FIG. 2, the drive member 6 is illustrated. Drive member 6 is configured to non-rotatably reside in each of the elongated apertures 17a and 17b. To this end, drive member 6 is complementary shaped to that of the elongated apertures 17a and 17b. In the illustrated embodiment, drive member 6 includes a generally rectangular shape; other shapes are contemplated. The drive member 6 is dimensioned such that respective interior walls 44a and 44b that define each of the elongated apertures 17a and 17b contact the drive member 6 from all sides to prevent the drive member 6 from rotating when the knob 14 is rotated. Thus, when the knob 14 is rotated, the drive member 6 is forced to translate along the longitudinal axis "A-A" instead of rotate thereabout.

A threaded aperture 42 of suitable proportion extends along a length of the drive member 6. In the illustrated embodiment, threaded aperture 42 extends the length of the drive member 6. The threaded aperture 42 of the drive member 6 is configured to operably couple the drive member 6 to the knob 14 and is configured to translate the drive member 6 including the reciprocating member 8 along the longitudinal axis "A-A."

Referring again to FIG. 2, the knob 14 is illustrated. Knob 14 threadably engages the drive member 6. More particularly, the elongated shaft 27 includes a threaded distal end 46 that operably couples to the elongated threaded aperture 44 of the drive member 6 (see FIG. 4 in combination with FIG. 5). As noted above, the elongated shaft 27 of the knob 14 is positioned through the openings 16 and 32 of respective proximal ends 12 and 26 of the handle 4 and the reciprocating member 8.

Knob 14 is rotatable about the longitudinal axis "A-A" and fixed from translation along the longitudinal axis "A-A." With this purpose in mind, an annular flange 48 is operably coupled to the elongated shaft 27 of the knob 14 and is disposed between the opening 32 at the proximal end 26 of the reciprocating member 8 and the opening 16 at the proximal end 12 of the handle 4, as best seen in FIG. 4. The annular flange 48 is configured to maintain the knob 14 in a fixed orientation along the longitudinal axis "A-A" while the knob 14 is rotated such that the drive member 6 is movable with respect to the knob 14 and along the longitudinal axis "A-A." To ensure that the knob 14 remains fixed along the longitudinal axis "A-A," the annular flange 48 includes a diameter that is greater than a diameter of the openings 16 and 32 of each of the proximal ends 12 and 26 of the handle 4 and the reciprocating member 8, respectively.

With reference to FIGS. 2 and 6, the plurality of cutting elements 10 is illustrated. The plurality of cutting elements 10 may be made from any suitable material. In embodiments, the material that the plurality of cutting elements 10 are made from is harder than the surgical rod material "R" is made from. For example, and in one particular embodiment, the plurality of cutting elements 10 is made from high-strength surgical stainless steel. The plurality of cutting elements 10 may be any suitable cutting elements known in the art. In the illustrated embodiments, the plurality of cutting elements 10 is in the form of six cutting wheels 10a-10f. While six cutting elements 10a-10f are described herein, it is within the purview of the present disclosure that any number of cutting wheels may be utilized, e.g., 3, 4, 5, 7, etc. The six cutting wheels 10a-10f provide an even score around surgical rod "R" with minimum rotation of the surgical rod scorer 2 about the surgical rod "R". As can be appreciated, this facilitates scoring surgical rod "R" in situ where the surgical environment is typically confined to a relatively small working space.

The plurality of cutting wheels 10a-10f may be disposed in any orientation on the operable end 22 of the handle 4 and distal end 28 of the reciprocating member 8. In the illustrated embodiment, the cutting wheels 10a-10c are evenly spaced apart from one another along a peripheral edge of the distal end 28 (FIG. 6). Likewise, the cutting wheels 10d-10f are evenly spaced apart from one another along a peripheral edge of the operable head 22 (FIG. 6).

The cutting wheels 10a-10f may have the same or different diameter. In the illustrated embodiment, cutting wheels 10b, 10d and 10f have the same diameter that is greater than a diameter of the remaining cutting wheels 10a, 10c and 10e that have the same diameter (FIG. 6). The larger diameter of the cutting wheels 10b, 10d and 10f provide a quicker and more thorough score of the surgical rod "R" when compared to the smaller cutting wheels 10a, 10c and 10e.

With reference to FIGS. 11-14, operation of the surgical rod scorer 2 is described in terms of use of a method for scoring surgical rod "R" in situ to remove an unwanted portion of the surgical "R."

Figures 12, 13:
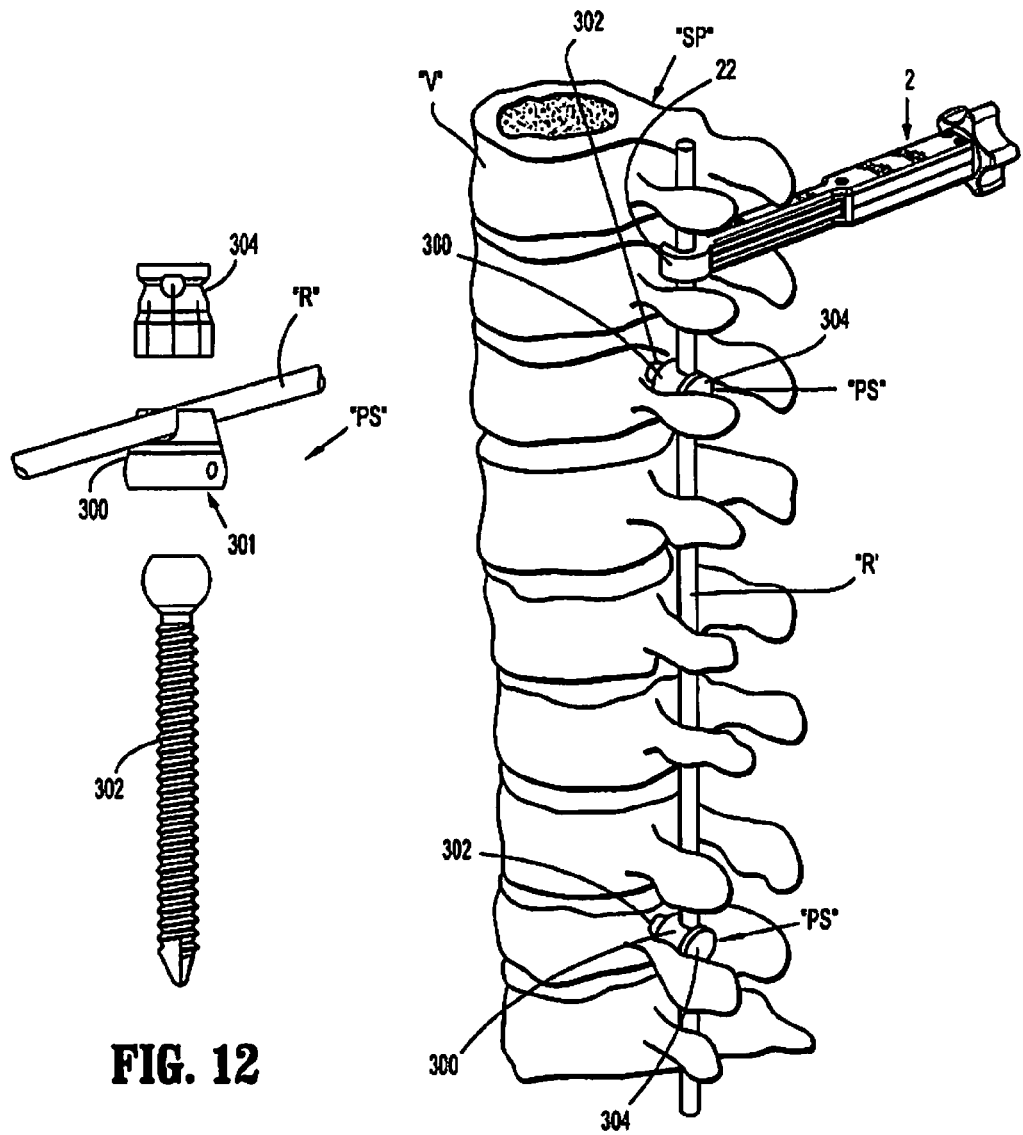
FIG. 12 is an isometric view of one of the pedicle screws depicted in FIG. 11 with a lock-nut unsecured thereto for receiving surgical rod thereabout subsequent to affixing the pedicel screw to the spine.
FIG. 13 is a perspective view of the surgical rod scorer depicted in FIG. 1 coupled to the surgical rod affixed to the spine depicted in FIG. 11.

Continuing with reference to FIGS. 11-14, the surgical rod "R" is affixed to a segment, e.g., vertebrae "V", of spine "SP" via at least two pedicle screw constructs "PS". One type of pedicle screw construct suitable for affixing surgical rod "R" to a spine "SP" is illustrated in FIG. 12. Pedicle screw construct "PS" is of the taper lock configuration and includes an outer housing or coupling 300 for receiving surgical rod "R" therethrough, a fixation or screw portion 302 for securing the pedicle screw construct "PS" to vertebrae "V" of the spine "SP," a locking structure in the form of a collet 304 for securing the surgical rod "R" to the body 300 of the pedicle screw construct "PS" and a pin 301 for aligning the collet 304 with the coupling 300. For a more detailed description of the pedicle screw construct "PS" and operative components associated therewith, reference is made to commonly-owned U.S. Patent Publication Number 2010/0262196 filed on Apr. 23, 2010 by Barrus et al., the entire contents of which being incorporated by reference herein.

While the surgical rod "R" is disclosed herein as being affixed to the spine "S" via two pedicle screws "PS," it is within the purview of the present disclosure that other types of bone anchors or bone anchoring systems may be utilized to affix the surgical rod "R" to the spine "SP." For example, and in one particular embodiment, a laminar hook or the like (not shown) may utilized to affix the surgical rod "R" to the spine "SP."

Figure 14:
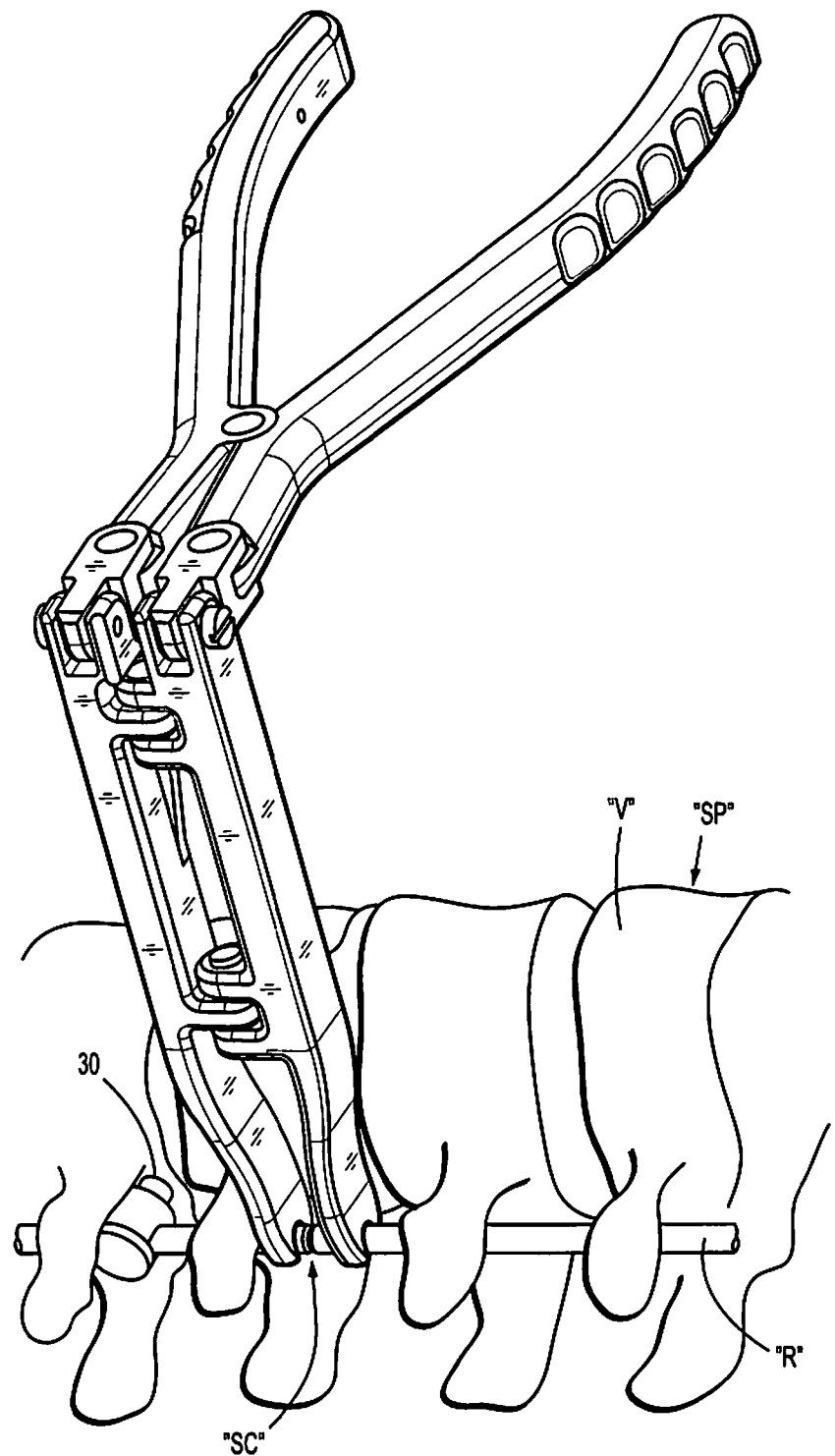
FIG. 14 is an enlarged, perspective view of the surgical instrument depicted in FIG. 9 attached to opposite sides of the scored surgical rod prior to bending the surgical to break the surgical rod at the scored portion.

Subsequent to securing the pedicle screw constructs "PS" to vertebrae "V" of the spine "SP" and securing the surgical rod "R" to the pedicle screw constructs "PS", a portion of the surgical rod "R" may need to be removed. For example, an end portion of the surgical rod "R" may extend past the body portion 300 of the pedicle screw construct "PS" and may need to be removed, as best seen in FIG. 14. Or, for example, a portion of the surgical rod "R" between two of the pedicle screw constructs "PS" may need to be removed. In either instance, other than the positioning of the surgical rod scorer 2 along a different portion of the surgical rod "R," the surgical rod scorer 2 is utilized in substantially the same manner. For illustrative purposes, the following description relates to removing an end portion of the surgical rod "R."

In one particular surgical scenario, to remove the unwanted end portion of the surgical rod "R," the reciprocating member 8 including the cutting elements 10a-10c, initially, is in the retracted position, see FIG. 7 for example. The operable head 22 of the surgical rod scorer 2 is placed or positioned around the surgical rod "R," see FIG. 13, for example. In one particular surgical scenario, the surgical rod "R" is placed through the notched opening 24 and positioned across the opening 29 of the operable head 22, see FIG. 4. Alternatively, and in one particular surgical scenario, the opening 29 of the operable head 22 may be mounted over an end of the surgical rod. Knob 14 is rotated, e.g., in a clockwise direction, which, in turn, translates the reciprocating member 8 including the cutting wheels 10a-10c distally to an extended position. Knob 14 is rotated until the edges of the cutting wheels 10a-10c contact the surgical rod "R" and force the surgical rod "R" into the edges of the cutting wheels 10d-10f.

The surgical rod scorer 2 is then rotated about the surgical rod "R". The amount or degree of rotation that the surgical rod scorer 2 is rotated or oscillated about the surgical rod "R" may depend on the type of surgical rod utilized, the type of spinal fixation device that the surgical rod "R" is attached to, the position of the spinal fixation device on a spine of the patient, etc. For illustrative purposes, it is assumed that the surgical rod scorer 2 is partially rotated 60° about the surgical rod "R". After each partial rotation of the surgical rod scorer 2 about the surgical rod "R", the knob 14 is further rotated, which, in turn, translates the reciprocating member 8 including the cutting elements 10a-10c distally to maintain contact between the plurality of cutting elements 10a-10f and the surgical rod "R" as scoring continues. This sequence of steps continues until the surgical rod "R" is scored to a desired depth. By way of example, when scoring a 5 or 6 millimeter solid titanium rod, one oscillation back and forth through approximately 60 degrees of arc, followed by further compression of the plurality of cutting elements 10a-10f against the surgical rod "R" and another oscillation back and forth through an approximate 60 degree arc should score the surgical rod "R" sufficiently to facilitate breaking off the surgical rod "R."

When the desired depth of the score of the surgical rod "R" is achieved, the knob 14 is rotated, e.g., in a counter-clockwise direction, which, in turn, translates the reciprocating member 8 including the cutting wheels 10a-10c proximally and back to the retracted position.

Figure 9:
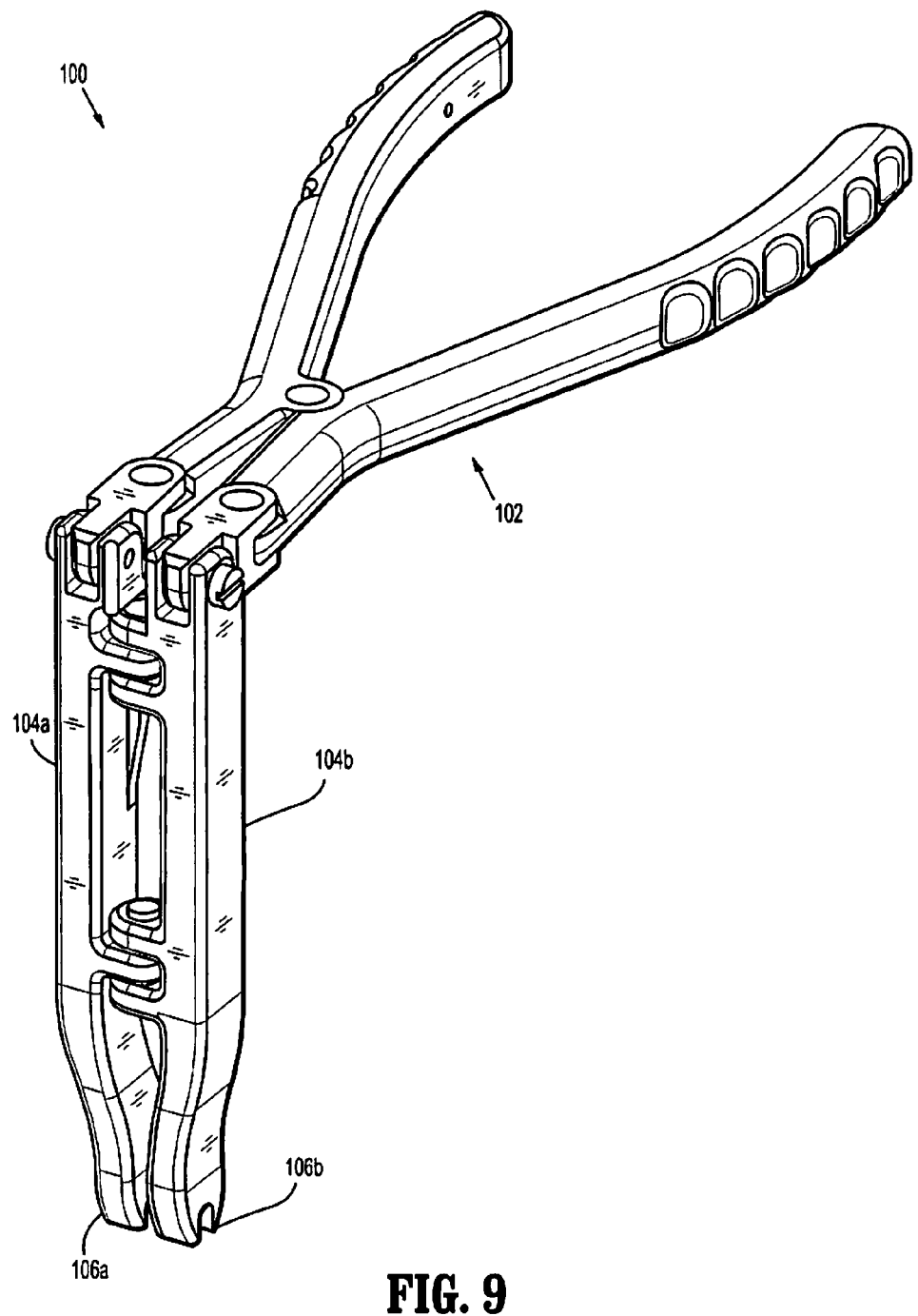
FIG. 9 is a perspective view of a surgical instrument configured for breaking surgical rod subsequent to scoring thereof.
Figure 10:
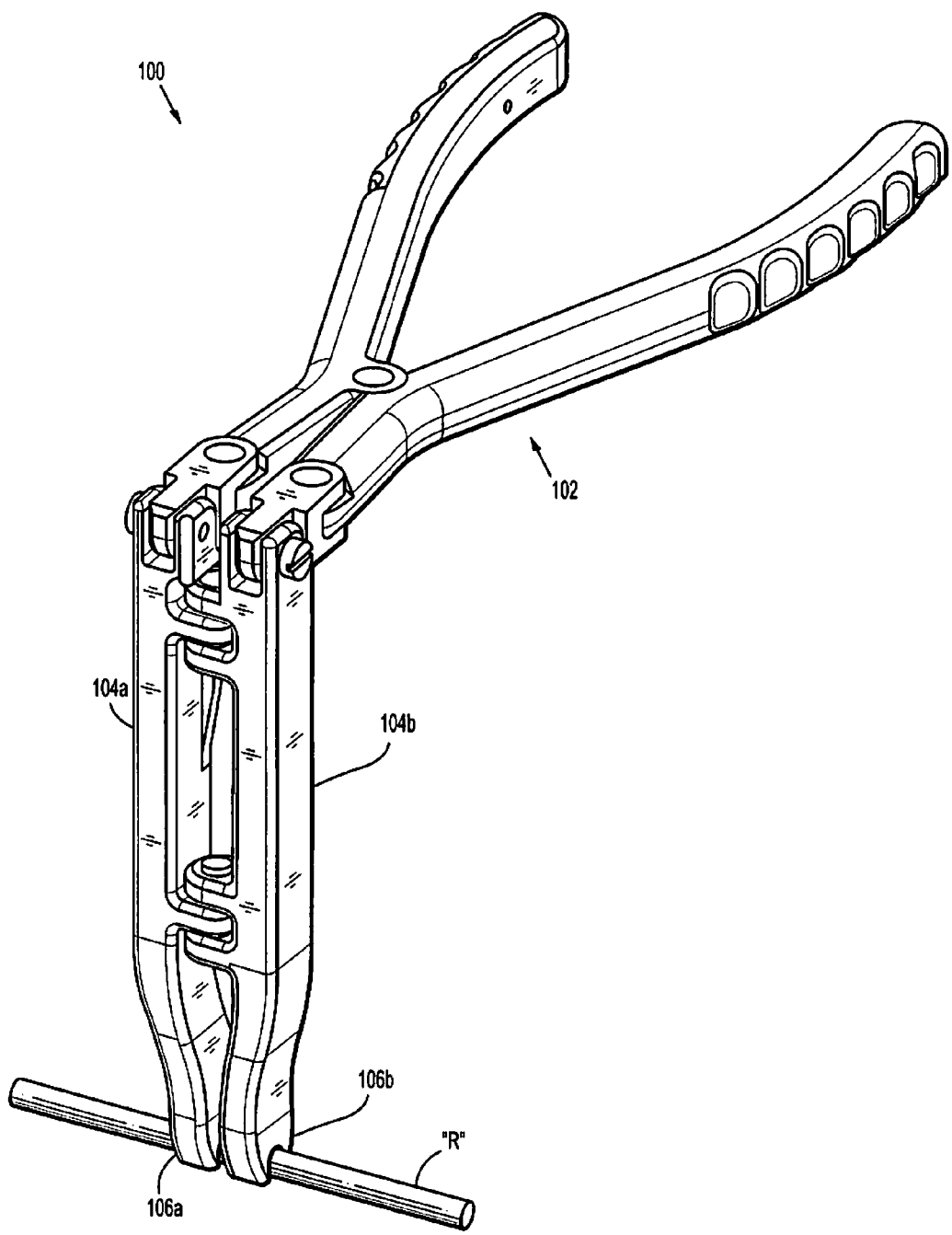
FIG. 10 is a perspective view of the surgical instrument depicted in FIG. 9 coupled to surgical rod that has been previously scored by one of the surgical rod scorers depicted in FIGS. 1 and 7.
Figure 11:
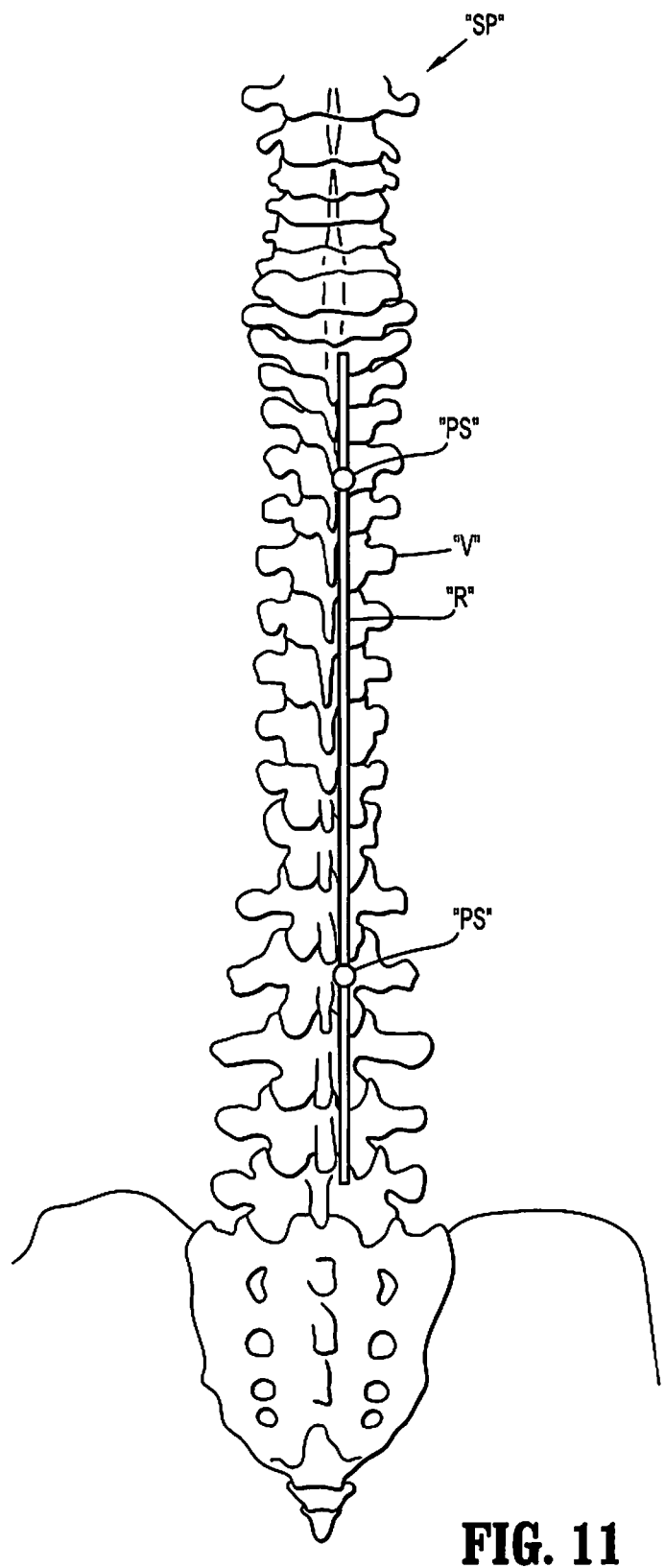
FIG. 11 is a schematic representation of a spine having a surgical rod affixed thereto via two pedicle screws.

A surgical rod bender 100 (FIG. 9) is utilized to grasp the scored surgical rod "R" on each side of the scored portion "SC" (see FIG. 14) of the surgical rod "R" (FIGS. 10 and 14). Surgical rod benders are common in the art. The surgical rod bender 100 illustrated in FIG. 9 includes a handle 102 that operably couples to two finger portions 104a and 104b having respective notched distal ends 106a and 106b that are configured to grasp surgical rod "R".

To cut or separate the scored surgical rod "R", the handle 102 of the surgical rod bender 100 is squeezed, which, in turn, moves the finger portions 104a and 104b away from one another. The scored surgical rod "R" separates along the scored portion of the surgical rod "R" when the fingers 104a and 104b have moved a predetermined distance away from one another.

As can be appreciated, the surgical rod scorer 2 according to the present disclosure overcomes some of the previously described shortcomings associated with the aforementioned devices utilized to cut or separate surgical rod "R". More particularly, scoring the surgical rod "R" initially and, subsequently, bending the scored surgical rod "R" across the scored portion reduces the shear forces needed to cut or separate the scored surgical rod "R" and, as a result thereof, provides a clean cut or separation of the surgical rod "R". Moreover, scoring the surgical rod "R" initially and, subsequently, bending the scored surgical rod "R" across the scored portion reduces and/or eliminates the likelihood of the cut or separated portion of the surgical rod "R" becoming a projectile that has to be recovered or retrieved.

From the foregoing and with reference to the various figure drawings, those skilled in the art will appreciate that certain modifications can also be made to the present disclosure without departing from the scope of the same. For example, in one particular embodiment, a surgical rod scorer 200 includes a modular type design (see FIGS. 7 and 8). Surgical rod scorer 200 is substantially identical to surgical rod scorer 2. In view thereof, only those features unique to surgical rod scorer 200 are described in detail.

For illustrative purposes, the surgical rod scorer 200 is described in terms of two main components, a handle 204 and an operable head 222. Handle 204 and operable head 222 are configured to releasably couple to one another. Each of the handle 204 and operable head 222 includes a respective handle half portion 204a and 204b and a reciprocating half portion 208a and 208b (FIG. 8).

By way of example, a tongue and groove configuration is utilized to operably couple the handle 204 to the operable head 222. More specifically, a groove 201 extends through a reciprocating member 208 and a shaft 220 of the handle 204 in a direction that is perpendicular to a longitudinal axis "B-B" that extends through the surgical rod scorer 200 (FIGS. 7 and 8). The groove 201 is collectively defined by handle half portions 204a and 204b and reciprocating half portions 208a and 208b. The groove 201 is configured to releasable couple to a corresponding tongue 203 that extends along a reciprocating member 208 and a shaft 220 of the operable head 222 in a direction that is perpendicular to a longitudinal axis "B-B." Tongue 203 is collectively defined by handle half portions 204a and 204b and reciprocating half portions 208a and 208b on the operable head 222.

To attach the operable head 222 to the handle 204, a user slides the tongue 203 through the groove 201 to a position that corresponds to the individual handle half portions 204a and 204b and reciprocating half portions 208a and 208b on the handle 204 aligning with the individual handle half portions 204a and 204b and reciprocating half portions 208a and 208b on the operable head 222. To facilitate coupling the tongue 203 and groove 201 to each other, the tongue 203 and groove 201 are tapered. This taper prevents the individual handle half portions 204a and 204b and reciprocating half portions 208a and 208b on the handle 204 from uncoupling from the individual handle half portions 204a and 204b and reciprocating half portions 208a and 208b on the operable head 222 when a knob 214 is rotated to return the individual handle half portions 204a and 204b and reciprocating half portions 208a and 208b on the handle 204 back to a retracted position.

To lock the handle 204 and operable head 222 to one another, a user rotates knob 214 until the reciprocating half portions 208a and 208b on the handle 204 push the reciprocating half portions 208a and 208b on the operable head 222 a predetermined distance distally at which time the operable head 222 is locked into place.

Once the operable head 222 is locked into place on the handle 204, the surgical rod scorer 200 may be operated in a manner as described above with respect to the surgical rod scorer 2. It is also contemplated that the handle and the operable head could be coupled together using a bayonet style mount assembly.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

For example, in the embodiment of FIGS. 1-6 the entire device could be entirely reusable or entirely disposable. Moreover, the plurality of cutting elements 10 can be entirely reusable or entirely disposable. In the embodiment of FIGS. 7 and 8, the entire device could be entirely reusable or entirely disposable, or, could be partially reusable or disposable.

It is contemplated that different operable heads 222 may be provided that are configured to couple to the handle 204 for cutting different surgical rods, rods of different material, or for different diameter rods.

It is contemplated, that the knobs 14/214 can be replaced with different types of motion. For example, instead of a rotatable knob 14/214, the knobs 14/214 may be configured for translation along the longitudinal axis "A-A." As a further alternative, a scissor type grip or pistol type grip that imparts longitudinal motion could be substituted for advancing the reciprocating member to assure contact between the cutting elements and the rod as scoring takes place. The handle could also include a ratchet mechanism to assure the continued application of force between the cutting elements and the rod as the cutting elements are advanced between oscillations of the device about the rod.

The invention claimed is:

1. A method for cutting a surgical rod in situ, comprising:
positioning an operable end of a surgical rod scorer around a surgical rod that has been previously affixed to a spinal segment via at least two bone anchors;
scoring a portion of the surgical rod with the surgical rod scorer;
grasping the scored surgical rod with a surgical rod bender such that grasping portions of the surgical rod bender are positioned on opposite sides of the scored portion;
removing the operable end from around the surgical rod; and
bending the scored surgical rod such that the surgical rod separates along the scored portion of the surgical rod.

2. A method for cutting surgical rod in situ according to claim 1, wherein the surgical rod scorer includes a plurality of cutting elements operably disposed thereon, at least one of the plurality of cutting elements translatable along a center-line of the surgical rod scorer from a retracted position, to an extended position for scoring the surgical rod.

3. A method for cutting surgical rod in situ according to claim 2, wherein the step of scoring the surgical rod includes the step of approximating a reciprocating member of the surgical rod scorer until the plurality of cutting elements contact the surgical rod.

4. A method for cutting surgical rod in situ according to claim 3, wherein the step of scoring includes the step of oscillating the surgical rod scorer about the surgical rod.

5. A method for cutting surgical rod in situ according to claim 4, wherein the step of oscillating includes oscillating the surgical rod scorer back and forth through approximately 60 degrees of an arc.

6. A method for cutting surgical rod in situ according to claim 5, wherein the step of scoring includes the step of compressing the plurality of cutting elements against the surgical rod followed by another oscillation back and forth through an approximate 60 degree arc, the sequencing of which continuing until a desired score depth is achieved.

7. A method for cutting surgical rod in situ according to claim 3, wherein the surgical rod scorer includes:
a handle having an elongated shaft extending therefrom defining a longitudinal axis; and
a knob supported on a proximal end of the handle, the knob rotatable about the longitudinal axis and axially stationary with respect to the longitudinal axis.

8. A method for cutting surgical rod in situ according to claim 7, wherein the operable end is disposed at a distal end of the elongated shaft configured to support at least one cutting element thereon, the operable end of the elongated shaft having an opening configured for insertion of the surgical rod therethrough.

9. A method for cutting surgical rod in situ according to claim 8, wherein the reciprocating member is operably disposed and axially translatable within the handle and the shaft of the surgical rod scorer, the reciprocating member including a proximal end in mechanical communication with the knob and a distal end configured to support at least one cutting element thereon.

10. A method for cutting surgical rod in situ according to claim 9, wherein a drive member is operably coupled to the proximal end of the reciprocating member and to the knob, wherein rotation of the knob about the longitudinal axis translates the reciprocating member including the at least one cutting element supported thereon from a retracted position, to an extended position for scoring the surgical rod inserted through the opening of the operable end of the shaft.

11. A method for cutting surgical rod in situ according to claim 10, wherein a distal end of an elongated shaft of the knob is threaded.

12. A method for cutting surgical rod in situ according to claim 11, wherein the proximal ends of each of the reciprocating member and the handle include an opening for receiving the elongated shaft therethrough.

13. A method for cutting surgical rod in situ according to claim 12, wherein an annular flange is operably coupled to the elongated shaft of the knob and is disposed between the opening at the proximal end of the reciprocating member and the opening at the proximal end of the handle, the annular flange configured to maintain the knob in a fixed orientation along the longitudinal axis while the knob is rotated such that the drive member is movable with respect to the knob and along the longitudinal axis.

14. A method for cutting surgical rod in situ according to claim 13, wherein the annular flange includes a diameter that is greater than a diameter of the openings of each of the proximal ends of the reciprocating member and the handle.

15. A method for cutting surgical rod in situ according to claim 14, wherein the distal end of the reciprocating member and the operable end of the shaft include a generally arcuate configuration to facilitate rotating the shaft including the reciprocating member about the surgical rod when surgical rod is positioned at the distal end of the shaft.

16. A method for cutting surgical rod in situ according to claim 15, wherein the at least one cutting element further comprises a plurality of cutting elements supported on each of the operable end of the shaft and the distal end of the reciprocating member are in the form of cutting wheels that rotatably seat within corresponding bushings operably coupled to each of the operable end of the shaft and the distal end of the reciprocating member, each of the bushings configured to facilitate rotation of the cutting wheels seated therein when the surgical rod scorer is rotated about surgical rod.

17. A method for cutting surgical rod in situ according to claim 1, wherein the at least two bone anchors are in the form of at least two pedicle screws.

18. A method for cutting a surgical rod in situ, comprising:
positioning an operable end of a surgical rod scorer around a surgical rod that has been previously affixed to a spinal segment via at least two bone anchors, the surgical rod scorer including a plurality of cutting elements operably disposed thereon, at least one of the plurality of cutting elements translatable along a center-line of the surgical rod scorer from a retracted position, to an extended position for scoring the surgical rod;

approximating a reciprocating member of the surgical rod scorer until the plurality of cutting elements contact the surgical rod;

scoring a portion of the surgical rod with the surgical rod scorer by oscillating the surgical rod scorer about the surgical rod back and forth through approximately 60 degrees of an arc;

grasping the scored surgical rod with a surgical rod bender such that grasping portions of the surgical rod bender are positioned on opposite sides of the scored portion; and bending the scored surgical rod such that the surgical rod separates along the scored portion of the surgical rod.

19. The method of claim 18 further comprising the step of removing the operable end from around the surgical rod before the step of bending the scored surgical rod.

20. The method of claim 18, wherein the step of scoring further includes compressing the plurality of cutting elements against the surgical rod after oscillating the surgical rod scorer about the surgical rod, followed by another oscillation back and forth through an approximate 60 degree arc, the sequencing of compressing and oscillating continuing until a desired score depth is achieved.

* * * * *